United States Patent [19]

Sivert

[11] Patent Number: 4,915,687

[45] Date of Patent: Apr. 10, 1990

[54] NEEDLELESS INJECTION PORT ARRANGEMENT

[76] Inventor: George A. Sivert, 7211 Columbia Ave., Louisville, Ky. 40222

[21] Appl. No.: 311,800

[22] Filed: Feb. 17, 1989

[51] Int. Cl.$^4$ .................. A61M 5/00; A61M 37/00
[52] U.S. Cl. .................. 604/83; 137/605; 251/149.1; 604/249
[58] Field of Search .......... 604/83, 82, 85, 236, 604/249, 33; 137/605; 251/149.1

[56] References Cited

U.S. PATENT DOCUMENTS

| | | | |
|---|---|---|---|
| 2,999,499 | 9/1961 | Willet | 604/83 |
| 3,276,472 | 10/1966 | Jinkens et al. | 604/83 |
| 3,416,567 | 12/1968 | Von Dardel | 604/83 |
| 3,994,293 | 11/1976 | Ferro | 604/83 |
| 4,252,116 | 2/1981 | Genese et al. | 604/83 |
| 4,601,701 | 7/1986 | Mueller, Jr. | 604/83 |

FOREIGN PATENT DOCUMENTS 0015443  9/1980  European Pat. Off. .......... 604/83

Primary Examiner—Stephen C. Pellegrino
Attorney, Agent, or Firm—Henderson & Sturm

[57] ABSTRACT

A needleless injection port arrangement (10) for intravenous fluid systems wherein the arrangement (10) includes a valving unit (12) disposed in a valve housing unit (11) having a dual port upper valve housing member (13): wherein, the valving unit (12) includes a valve head member (50) mounted on a resilient biasing member (40) to control the introduction of medicant fluids through a medicant fluid port (18) formed in the upper valve housing member (13).

8 Claims, 1 Drawing Sheet

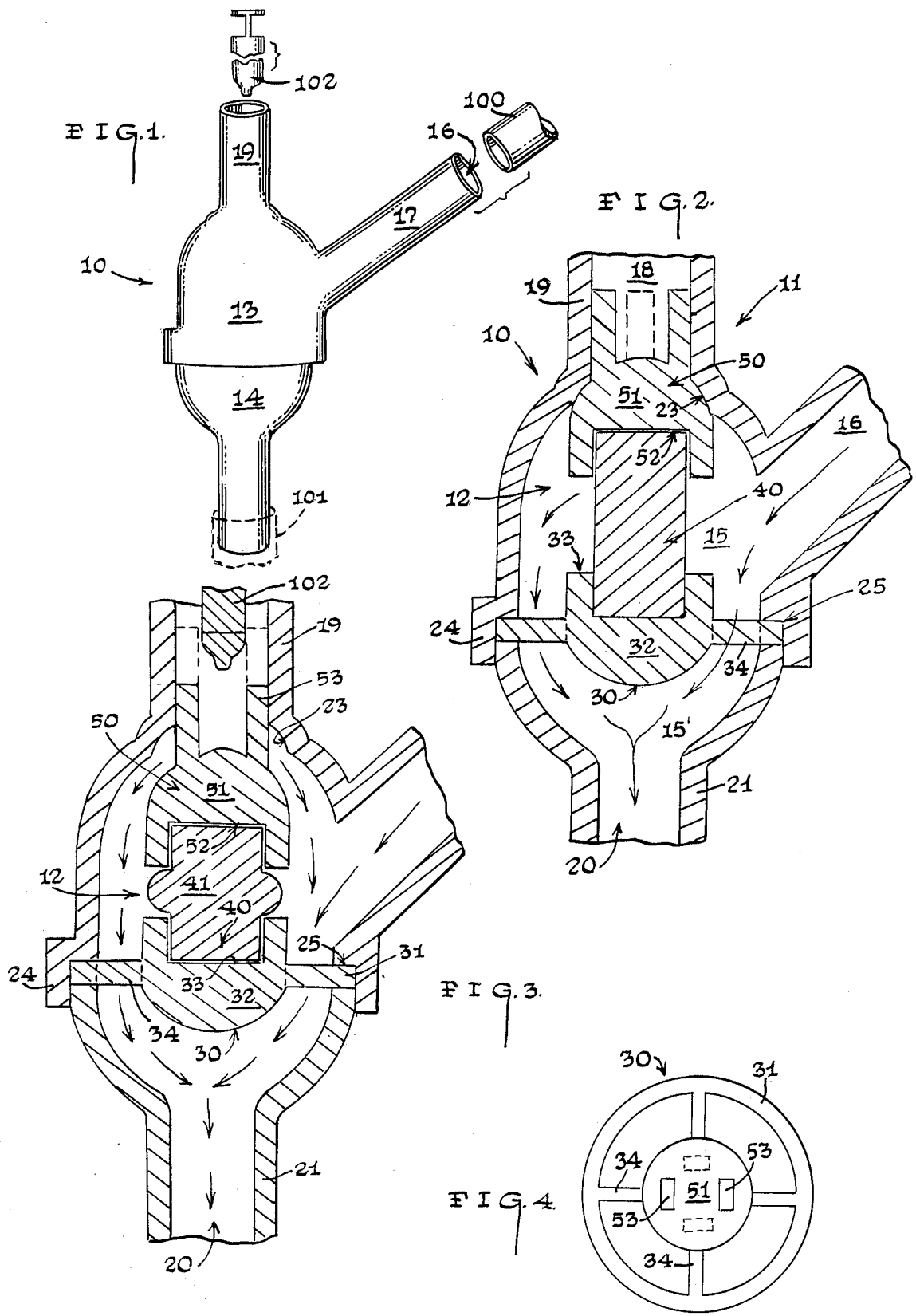

NEEDLELESS INJECTION PORT ARRANGEMENT

TECHNICAL FIELD

The present invention relates to medical valves in general, and more particularly to valving arrangements that allow medicants to be intermittently or continuously intravenously introduced into a patients bloodstream without the necessity of subjecting the patient to repeated injections.

BACKGROUND OF THE INVENTION

This invention was the subject matter of Document Disclosure Program Registration No. 194,220 which was filed in the U. S. Pat. and Trademark Office on May 31, 1988.

As can be seen by reference to the following U.S. Pat. No's: 4,601,701; 3,276,472; 4,252,116; and, 2,999,499 the prior art is replete with myriad and diverse arrangements for administering a variety of medicants to a patient in both a simultaneous and/or sequential fashion.

While all of the aforementioned prior art constructions are more than adequate for their intended purpose and function, most of these inventions were developed prior to the onset of the current AIDS epidemic; and as such these inventions were not particularly concerned with the problems that face the vast majority of medical professionals in todays environment.

Given the fact that the AIDS virus can be transmitted by contact with contaminated needles or exposure to blood which contains the virus, todays health care professionals are particularly wary of procedures involving injections for the purpose of introducing medicants or withdrawing blood from a patient.

Considering the fact that every injection that is administered to a patient hypothetically runs the risk of infecting the recipient and/or the person administering the injection with the AIDS virus; it should not come as a surprise that medical professionals welcome with open arms any procedure that minimizes the number of times that they are potentially exposed to infections of any type.

In light of the foregoing situation there has existed a long standing need among medical professionals for a new valving arrangement that will allow medicants to be introduced into an intravenous fluid delivery system with minimum likelihood that the medicant dispensing needle will come into contact with either the patient or the individual giving the injection; and, the provision of such an arrangement is a stated objective of the present invention.

SUMMARY OF THE INVENTION

Briefly stated, the needless injection port arrangement that forms the basis of the present invention comprises a valve housing unit and a valving unit suspended within the valve housing unit.

The valve housing unit comprises in general a dual port upper valve housing member and a single port lower valve housing member; wherein, the dual ports in the upper valve housing member are adapted to be connected to a source of intravenous fluid and a source of liquid medicants respectively. In addition, one of the dual ports is further provided with a valve seat which will be described in greater detail further on in the specification.

The valve unit of this invention comprises in general: a valve support member disposed intermediate the upper and lower valve housing members; a resilient biasing member having one end engaged with the valve support member; and, a valve head member engaged on one end with the other end of the resilient biasing member and having its other end adapted to releasably engage the valve seat in the upper housing member.

In addition, all of the components that comprise the needleless injection port arrangement of this invention are fabricated from chemically inert and stesrilizable material; and, the components that form the valve unit are dimensioned such that they cannot pass through any of the ports in the valve housing unit.

BRIEF DESCRIPTION OF THE DRAWINGS

These and other objects, advantages and novel features of the invention will become apparent from the detailed description of the best mode for carrying out the preferred embodiment of the invention which follows; particularly when considered in conjunction with the accompanying drawings, wherein:

FIG. 1 is a perspective view of the needless injection port arrangement of this invention;

FIG. 2 is a cross-section view of the arrangement in the closed position;

FIG. 3 is a cross-sectional view of the arrangement in the open position; and,

FIG. 4 is an isolated top plan view of the valve head member and a portion of the valve support member.

BEST MODE FOR CARRYING OUT THE INVENTION

As can best be seen by reference to the drawings and in particular to FIGS. 1 and 2, the needleless injection port arrangement that forms the basis of the present invention is designated generally by the reference numeral (10). The arrangement (10 comprises in general a valve housing unit (11) and a valving unit (12).

As shown in FIGS. 1 thru 3, the valve housing unit (11) comprises a dual port upper housing member (13) and a single port (13) defines an enlarged fluid chamber (15) which is in open fluid communication with an intravenous fluid port (16) formed in a first generally cylindrical hollow tubular projection (17) formed in the upper housing member (13); and, a medicant fluid port (18) formed in a second generally cylindrical hollow tubular projection (19).

In addition, the single port lower housing member (14) also defines an enlarged fluid chamber (15') which is in open communication with the enlarged fluid chamber (15) of the upper housing member (13); and, the lower housing member (14) is further provided with a fluid outlet port (20) formed in a third generally cylindrical hollow tubular projection (21) formed in the housing unit (11).

As can best be seen by reference to FIGS. 2 and 3, the upper valve housing member (13) is provided with an arcuate valve seat (23) which surrounds the outlet of the medicant fluid port (18). In addition, the upper valve housing member (13) is further provided with an enlarged skirt portion (24) on its lower end; wherein, the skirt portion (24) is provided with a stepped shoulder recess (25) that is dimensioned to receive and frictionally engage the upper periphery of the lower valve housing member (14) in a well recognized fashion.

Turning now particularly to FIGS. 2 thru 4, it can be appreciated that the valving unit (12) comprises a valve support member (30); a resilient biasing member (40) and a valve head member (50). The valve support member (30) comprises in general: an outer support ring element (31) which is dimensioned to be captively engaged in the recess (25) formed in the upper (13) housing member; an enlarged inner support element (32) having a generally cylindrical central recess (33) formed therein; and a plurality of spaced radially disposed support arm elements (34) which operatively secure the inner support element (33) to the outer support ring element (31).

The resilient biasing member (40) comprises in general: an elongated generally cylindrical resilient plug element (41) fabricated from resilient deformable material, such as rubber or the like; wherein, the lower end f the plug element is dimensioned to be received within and supported by the central recess (33) in the inner support element (32) of the valve support member (30).

The valve head member (50) as depicted in FIGS. 2 thru 4 comprises an enlarged generally circular valve head element (51) having a central recess (52) formed in its lower end and a plurality of guide arms (53) projecting from its upper end. The central recess (52) in the valve head member (50) is dimensioned and designed to receive and be supported by the resilient biasing member (40).

In addition, the outer periphery of the guide arms (53) are given an arcuate configuration such that the guide arms (53) will be slidingly received in the medicant fluid port (18); and, the arcuate periphery of the generally circular valve head element (51) will conform to the arcuate valve seat (23) which surrounds the outlet of the medicant fluid port (18).

As can best be seen by reference to FIG. 1, the needleless injection port arrangement (10) of this invention is intended for use in an intravenous fluid system wherein an upstream intravenous fluid supply tube (100) is connected to the intravenous fluid port (16) and the fluid outlet port (21) is connected to a downstream intravenous fluid supply tube (101) shown in phantom.

Turning now to FIGS. 2 and 3, it can be appreciated that when it is desired to introduce medicant fluids into the arrangement (10), the medical professional merely has to insert a syringe (102) into the medicant fluid port (18) formed in the second generally cylindrical hollow tubular projection (19) in the upper housing member (13). The tip of the syringe will contact the guide arms (53) of the valve head element (51); to displace the valve head element (51) away from the valve seat (23) against the resistance of the resilient biasing member (40) to allow liquid medicants to be introduced into the intravenous fluid flow.

Having thereby described the subject matter of this invention it should be apparent that many substitutions, modifications, and variations of the invention are possible in light of the above teachings. It is therefore to be understood that the invention as taught and described herein is only to be limited to the extent of the breadth and scope of the appended claims.

I claim:

1. A needleless injection port arrangement adapted for use in an intravenous fluid system including an upstream intravenous fluid supply tube, a downstream intravenous fluid supply tube, and a syringe containing fluid medicants wherein said arrangement comprises:

a valve housing unit disposed intermediate both the upstream and downstream intravenous supply tubes wherein the valve housing unit comprises a dual port upper valve housing member operatively connected to a single port lower valve housing member; and, a valving unit operatively disposed intermediate the upper and the lower valve housing members wherein the valving unit comprises: a valve support member captively engaged between the upper and the lower valve housing members and having a central recess formed therein; a resilient biasing member having one end dimensioned to be received and supported in said central recess; and, a valve head member having a central recess formed in the lower end; wherein, the central recess in the valve head member is dimensioned to receive the other end of said resilient biasing member.

2. The arrangement as in claim 1 wherein said upper valve housing member is provided with an enlarged fluid chamber which is in open communication with an intravenous fluid port formed in a first generally cylindrical hollow tubular projection; and, a medicant fluid port formed in a second generally cylindrical hollow tubular projection.

3. The arrangement as in claim 2 wherein the periphery of said medicant fluid port is provided with an arcuate valve seat that is dimensioned to sealingly contact the upper portion of said valve head member.

4. The arrangement as in claim 3 wherein the valve head member is provided on the upper portion with a plurality of guide arms which are dimensioned to be slidingly received in said medicant fluid port.

5. The arrangement as in claim 4 wherein the base of the upper valve housing member is provided with an enlarged skirt having a stepped shoulder recess that is dimensioned to receive and sealingly engage the upper portion of the lower valve housing member.

6. The arrangement as in claim 5 wherein the resilient biasing member comprises:

an elongated generally cylindrical resilient plug element.

7. The arrangement as in claim 1 wherein the lower valve housing member is further provided with a fluid outlet port formed in a third generally cylindrical hollow tubular projection formed in the said housing unit.

8. The arrangement as in claim 7 wherein said fluid outlet port is dimensioned such that the fluid outlet port will prevent the passage of the valve head member, the valve support member, and the resilient biasing member through the lower valve housing member.

* * * * *